(12) United States Patent
Zhu et al.

(10) Patent No.: US 11,845,781 B2
(45) Date of Patent: Dec. 19, 2023

(54) FUSION PROTEIN COMPRISING FIBROBLAST GROWTH FACTOR 19 (FGF 19) AND GLUCAGON-LIKE PEPTIDE-1

(71) Applicant: Jiangnan University, Wuxi (CN)

(72) Inventors: Shenglong Zhu, Wuxi (CN); Yongquan Chen, Wuxi (CN); Zhen Wang, Wuxi (CN)

(73) Assignee: JIANGNAN UNIVERSITY, Wuxi (CN)

(*) Notice: Subject to any disclaimer, the term of this patent is extended or adjusted under 35 U.S.C. 154(b) by 0 days.

(21) Appl. No.: 18/181,666

(22) Filed: Mar. 10, 2023

(65) Prior Publication Data

US 2023/0265141 A1    Aug. 24, 2023

Related U.S. Application Data

(63) Continuation of application No. PCT/CN2022/071528, filed on Jan. 12, 2022.

(30) Foreign Application Priority Data

Apr. 30, 2021 (CN) .......................... 202110499380.8

(51) Int. Cl.
| | | |
|---|---|---|
| *C07K 14/50* | (2006.01) | |
| *A61P 3/04* | (2006.01) | |
| *A61P 3/06* | (2006.01) | |
| *A61P 3/10* | (2006.01) | |
| *C07K 14/605* | (2006.01) | |
| *A61K 38/00* | (2006.01) | |

(52) U.S. Cl.
CPC ................ *C07K 14/50* (2013.01); *A61P 3/04* (2018.01); *A61P 3/06* (2018.01); *A61P 3/10* (2018.01); *C07K 14/605* (2013.01); *A61K 38/00* (2013.01); *C07K 2319/31* (2013.01)

(58) Field of Classification Search
CPC ........ C07K 14/50; C07K 2319/31; A61P 3/10
See application file for complete search history.

(56) References Cited

U.S. PATENT DOCUMENTS

2013/0129724 A1* 5/2013 Boettcher .............. C07K 14/50
424/134.1

FOREIGN PATENT DOCUMENTS

| CA | 2764835 | * | 12/2010 |
|---|---|---|---|
| CN | 1560249 A | | 1/2005 |
| CN | 101993496 A | | 3/2011 |
| CN | 107108711 A | | 8/2017 |
| CN | 110028587 A | | 7/2019 |
| WO | 0188209 A1 | | 11/2001 |

* cited by examiner

*Primary Examiner* — Gyan Chandra
(74) *Attorney, Agent, or Firm* — IPRO, PLLC; Na Xu (57) ABSTRACT

The present disclosure discloses a preparation method and use of a double-target fusion protein, and belongs to the technical field of medicines. According to the present disclosure, a novel fusion protein is obtained by transforming an FGF19 sequence and fusing the FGF19 sequence with GLP-1. Compared with wild-type FGF19 and GLP-1, the novel fusion protein has a more long-acting and stable effect, further reduces the carcinogenic risk of FGF19, and can better relieve liver damage and correct metabolic disorder, obesity, overweight, metabolic syndrome, diabetes, dyslipidemia and other diseases. Besides, in treatment, there are no side effects of gastrointestinal discomforts such as diet decline caused by GLP-1 treatment. Therefore, the double-target fusion protein has a wide application prospect.

12 Claims, 4 Drawing Sheets

Specification includes a Sequence Listing.

SEQUENCE LISTING

```
Sequence total quantity: 12
SEQ ID NO: 1           moltype = AA  length = 183
FEATURE                Location/Qualifiers
source                 1..183
                       mol_type = protein
```

```
                             organism = synthetic construct
SEQUENCE: 1
VHYGWGDPIR LRHLYTSGPH GLSSCFLRIR ADGVVDCARG QSAHSLLEIK AVALRTVAIK       60
GVHSVRYLCM GADGKMQGLL QYSEEDCAFE EEIRPDGYNV YRSEKHRLPV SLSSAKQRQL      120
YKNRGFLPLS HFLPMLPMVP EEPEDLRGHL ESDMFSSPLE TDSMDPFGLV TGLEAVRSPS      180
FEK                                                                    183

SEQ ID NO: 2             moltype = AA  length = 171
FEATURE                  Location/Qualifiers
source                   1..171
                         mol_type = protein
                         organism = synthetic construct
SEQUENCE: 2
VHYGWGDPIR LRHLYTSGPH GLSSCFLRIR ADGVVDCARG QSAHSLLEIK AVALRTVAIK       60
GVHSVRYLCM GADGKMQGLL QYSEEDCAFE EEIRPDGYNV YRSEKHRLPV CLSSAKQRQL      120
YKNRGFLPLP GLPPALPEPP GILAPQPPDV GSSDPLSMVG PSQGRSPSYA S               171

SEQ ID NO: 3             moltype = AA  length = 182
FEATURE                  Location/Qualifiers
source                   1..182
                         mol_type = protein
                         organism = synthetic construct
SEQUENCE: 3
VHYGWGDPIR LRHLYTSGPH GLSSCFLRIR ADGVVDCARG QSAHSLLEIK AVALRTVAIK       60
GVHSVRYLCM GADGKMQGLL QYSEEDCAFE EEIRPDGYNV YRSEKHRLPV CLSSAKQRQL      120
YKNRGFLPLC HFLPMLPMVP EEPEDLRGHL ESDMFSSPPD VGSSDPLSMV GPSQGRSPSY      180
AS                                                                     182

SEQ ID NO: 4             moltype = AA  length = 31
FEATURE                  Location/Qualifiers
source                   1..31
                         mol_type = protein
                         organism = synthetic construct
SEQUENCE: 4
HAEGTFTSDV SSYLEGQAAK EFIAWLVRGR G                                      31

SEQ ID NO: 5             moltype = AA  length = 39
FEATURE                  Location/Qualifiers
source                   1..39
                         mol_type = protein
                         organism = synthetic construct
SEQUENCE: 5
HGEGTFTSDL SKQMEEEAVR LFIEWLKNGG PSSGAPPPS                              39

SEQ ID NO: 6             moltype = AA  length = 214
FEATURE                  Location/Qualifiers
source                   1..214
                         mol_type = protein
                         organism = synthetic construct
SEQUENCE: 6
HAEGTFTSDV SSYLEGQAAK EFIAWLVRGR GVHYGWGDPI RLRHLYTSGP HGLSSCFLRI       60
RADGVVDCAR GQSAHSLLEI KAVALRTVAI KGVHSVRYLC MGADGKMQGL LQYSEEDCAF      120
EEEIRPDGYN VYRSEKHRLP VSLSSAKQRQ LYKNRGFLPL SHFLPMLPMV PEEPEDLRGH      180
LESDMFSSPL ETDSMDPFGL VTGLEAVRSP SFEK                                  214

SEQ ID NO: 7             moltype = AA  length = 202
FEATURE                  Location/Qualifiers
source                   1..202
                         mol_type = protein
                         organism = synthetic construct
SEQUENCE: 7
HAEGTFTSDV SSYLEGQAAK EFIAWLVRGR GVHYGWGDPI RLRHLYTSGP HGLSSCFLRI       60
RADGVVDCAR GQSAHSLLEI KAVALRTVAI KGVHSVRYLC MGADGKMQGL LQYSEEDCAF      120
EEEIRPDGYN VYRSEKHRLP VCLSSAKQRQ LYKNRGFLPL PGLPPALPEP PGILAPQPPD      180
VGSSDPLSMV GPSQGRSPSY AS                                               202

SEQ ID NO: 8             moltype = AA  length = 213
FEATURE                  Location/Qualifiers
source                   1..213
                         mol_type = protein
                         organism = synthetic construct
SEQUENCE: 8
HAEGTFTSDV SSYLEGQAAK EFIAWLVRGR GVHYGWGDPI RLRHLYTSGP HGLSSCFLRI       60
RADGVVDCAR GQSAHSLLEI KAVALRTVAI KGVHSVRYLC MGADGKMQGL LQYSEEDCAF      120
EEEIRPDGYN VYRSEKHRLP VCLSSAKQRQ LYKNRGFLPL CHFLPMLPMV PEEPEDLRGH      180
LESDMFSSPP DVGSSDPLSM VGPSQGRSPS YAS                                   213

SEQ ID NO: 9             moltype = AA  length = 190
FEATURE                  Location/Qualifiers
```

```
source          1..190
                mol_type = protein
                organism = synthetic construct
SEQUENCE: 9
MRDSSPLVHY GWGDPIRLRH LYTSGPHGLS SCFLRIRADG VVDCARGQSA HSLLEIKAVA    60
LRTVAIKGVH SVRYLCMGAD GKMQGLLQYS EEDCAFEEEI RPDGYNVYRS EKHRLPVSLS   120
SAKQRQLYKN RGFLPLSHFL PMLPMVPEEP EDLRGHLESD MFSSPLETDS MDPFGLVTGL   180
EAVRSPSFEK                                                          190

SEQ ID NO: 11       moltype = DNA   length = 642
FEATURE             Location/Qualifiers
source              1..642
                    mol_type = other DNA
                    organism = synthetic construct
SEQUENCE: 10
cacgctgaag gcaccttcac ttctgacgtt tcctcttacc tggaaggcca ggctgcgaaa    60
gaattcatcg cgtggctggt gcgcggtcgt ggtgttcact acggttgggg tgatccgatc   120
cgtctgcgtc atctgtatac cctctggcccg catggtctgc cttcctgctt tctgcgcatc   180
cgtgctgatg gtgtggtaga ttgcgcacgt ggtcagtccg cgcactccct gctggaaatc   240
aaagctgttg ctctgcgtac cgttgccatc aaaggcgtcc acagcgttcg ttatctgtgt   300
atgggcgctg atggcaaaat gcagggtctg ctgcaatact ctgaagaaga ttgtgctttc   360
gaagaggaaa ttcgtccgga cggctataac gtgtatcgct ccgaaaagca ccgtctgccg   420
gtttctctgt ctagcgctaa acagcgtcag ctgtacaaaa accgcggctt tctgcctctg   480
tctcacttcc tgcctatgct gccgatggtg ccggaagaac cggaagacct gcgcggccac   540
ctggaatctg acatgttctc ctccccgctg gagactgaca gcatggaccc gttcggtctg   600
gtgactggtc tggaagcagt tcgctccccg tctttcgaga ag                      642

SEQ ID NO: 11       moltype = DNA   length = 606
FEATURE             Location/Qualifiers
source              1..606
                    mol_type = other DNA
                    organism = synthetic construct
SEQUENCE: 11
cacgctgaag gcactttttac tagcgatgta tcttcctacc tggaaggtca ggcggctaaa   60
gagtttattg cgtggctggt tcgtggtcgc ggcgtccact acggttgggg cgacccgatc   120
cgtctgcgcc acctgtatac ttctggtccg cacggcctgt cttcttgttt tctgcgtatc   180
cgcgcagacg tgttgtgga ttgtgctcgt ggccagtctg cgcactctct gctggaaatc   240
aaagcggtgg cactgcgtac ggtggctatc aaaggcgtac atagcgtccg ttacctgtgc   300
atgggtgcgg atggtaaaat gcagggtctg ctgcagtact ccgaagaaga ttgtgcgttc   360
gaagaagaaa tccgcccgga tggttacaac gtataccgtt ctgaaaaaca ccgtctgccg   420
gtttgcctga gctctgcgaa acagcgtcag ctgtacaaaa accgtggctt cctgccgctg   480
ccgggtctgc cgccagcact gccggaaccg cctggtatcc tggctccgca gccgccagat   540
gtaggcagct ccgacccact gtccatggtt ggtccgtccc agggtcgtag cccgtcttac   600
gcatct                                                              606

SEQ ID NO: 12       moltype = DNA   length = 639
FEATURE             Location/Qualifiers
source              1..639
                    mol_type = other DNA
                    organism = synthetic construct
SEQUENCE: 12
catgcagaag gtaccttttac ttctgatgtc tcctcctatc tggaaggtca ggcagccaaa    60
gaattcatcg catggctggt tcgtggtcgt ggtgtgcatt acggttgggg cgacccgatc   120
cgcctgcgtc acctgtacac cagcggtccg cacggcctga gctcctgttt tctgcgtatc   180
cgcgcagacg gcgtggtgga ttgcgcgcgc ggccagtccg cacatagcct gctggaaatt   240
aaagccgttg cactgcgtac cgtggcgatc aaaggtgttc actccgtccg ttacctgtgt   300
atgggcgcgg acggtaagat gcagggtctg ctgcagtact ctgaggaaga ttgcgcgttc   360
gaagaagaaa tccgtccaga cggctataac gtgtaccgta gcgagaaaca ccgtctgccg   420
gtttgcctga gctccgcaaa acagcgtcag ctgtataaaa accgtggctt tctgccgctg   480
tgtcatttcc tgccgatgct gccgatggta ccggaagaac cggaagacct gcgcggtcac   540
ctggaatctg acatgttttc ctctccaccg gatgttggta gcagcgaccc actgtccatg   600
gtgggcccga gccagggccg ttccccgagc tacgcatct                          639
```

FUSION PROTEIN COMPRISING FIBROBLAST GROWTH FACTOR 19 (FGF 19) AND GLUCAGON-LIKE PEPTIDE-1

REFERENCE TO SEQUENCE LISTING

The instant application contains a Sequence Listing in XML format as a file named "YGHY-2022-87 seq.xml", created on Feb. 27, 2023, of 14 kB in size, and which is hereby incorporated by reference in its entirety.

Technical Field

The present disclosure relates to a preparation method and use of a double-target fusion protein, and belongs to the technical field of medicines.

Background

Fibroblast growth factor-19 (FGF19) is a newly discovered metabolic regulatory factor that stimulates intestinal secretion and expression after bile acid is secreted into the intestinal tract. FGF19 can enter liver along with circulation after secreted by the intestinal tract and works in combination with FGFR4 in liver. It has a hormone-like effect and plays important roles in metabolic regulations, such as regulating bile acid metabolism, regulating gallbladder filling, improving energy metabolism, reducing body mass, ameliorating blood sugar and the like. Since several previous studies show that FGF19 has a mitogenic effect, FGFR4 can promote proliferation of FGF19 in the liver and has a carcinogenic effect. In 2014, an N-terminal domain of FGF19 was found to be a region essential for interaction with FGFR. Therefore, selective knockout of a region recognizing a FGFR4 receptor can eliminate the mitogenic activity of FGF19. A plurality of articles focused on mutations at the N-terminal of FGF19.

NGM282 is a non-tumorigenic engineered mutant obtained by mutation at an N-terminal of human FGF19. A phase II clinical study on NGM282 has just completed in the United States. The results show that 79% of patients reach a primary treatment endpoint and 34% of patients reach the normal liver fat content at 12 weeks. The mutant improves serum biomarkers of liver function, lipid metabolism, and fibrosis of patients, and shows a curative effect of treating metabolic diseases. However, in addition to some common digestive tract symptoms, nausea, and erythema at an injection site, FGF19 mutant NGM282 is also found to significantly increase cholesterol content after injection in the above clinical study. Besides, many studies show that the increased cholesterol content is one of the significantly high-risk factors for metabolic diseases, which is a huge risk for the treatment of the metabolic diseases. In addition, FGF19 also causes symptoms such as anorexia, appetite reduction and the like, and has certain hidden troubles for a future treatment process.

Glucagon-like peptide-1 (GLP-1), as a product of post-translational processing of a proglucagon gene was first discovered in 1984 (MajaovS et al, JBiolchem, 1986, 261: 11880-11889). In L cells of the intestinal tract, proglucagon is cleaved into glucagon-like peptide-1 (GLP-1), glucagon-like peptide-2 (GLP-2) and glucagon (NielsenLL et al, RegulPept, 2004, 117: 77-88). GLP-1 initially produced in the intestinal tract is inactive 37 peptide, which needs 6 peptide cleavage at an N-terminal to form biologically active GLP-1 (7-37) is formed. GLP-1 (7-37) can be degraded into a GLP-1(7-36) amide form with C-terminal glycine thereof as a substrate for amidating enzyme. The C-terminal amidation increases the stability of GLP-1 in vivo. About 80% of the naturally produced GLP-1 exists in the intestinal tract in the latter form (KiefferTJ et al, EndocrRev, 1999, 25: 876-913). During a digestion and absorption process in the intestinal tract, food stimulates L cells of the intestinal tract to secrete GLP-1, in which carbohydrates and lipids have the strongest stimulation effect. Within 5-30 minutes after meals of normal people, GLP-1 concentration in blood plasma is significantly increased. As an important incretin, GLP-1 has the following main biological functions: (1) binding to a specific receptor GLP-1R on an islet I cell to stimulate the generation and release of insulin; (2) reducing body weight; (3) ameliorating lipid metabolism disorders; and (4) reducing a gastric emptying rate and suppressing appetite (Vaidya, HB et al, CurrDrugTargets, 2008, 9: 911-92).

Although natural GLP-1 has a plurality of advantages in treating diabetes and improving blood fat, it has a short half-life period in plasma in vivo, which limits its direct clinical use. In-vivo dipeptidylpeptidase IV (DPPIV) can specifically recognize an Ala residue at a second position of an N-terminal of GLP-1, a dipeptide is cut from the N-terminal of a peptide chain, such that GLP-1 is quickly degraded into inactive GLP-1(9-36) and GLP-1(9-37) in vivo, with a biological half-life period of only about 2 minutes.

Therefore, although the research on GLP-1 is deeper at present and the research on the structure and function thereof is relatively sufficient, it still has a short half-life, which still inhibits its further role. Besides, as a newly discovered metabolic regulatory factor, notwithstanding the effect of reducing liver fat, FGF19 increases the cholesterol content in serum, which causes other damages to the body and also prevents further use.

SUMMARY

In order to solve the problems of a short half-life period of GLP-1 and a great side effect of FGF19 at present, the inventor modifies amino acid sequences of GLP-1 and FGF19 and fuses the amino acid sequences to reduce the side effects of the two, such as the short half-life period of the GLP-1, increase a blood sugar-reducing effect of FGF19, reduce the function of increasing high cholesterol, and further reduce the carcinogenic risk of FGF19.

The present disclosure provides a fusion protein containing GLP-1 or an analog thereof, exendin-4, and a human FGF19 mutant. The fusion protein is prepared and produced by a recombinant DNA technology. As a therapeutic drug or a pharmaceutical composition, the fusion protein can be used for treating diseases related to hyperglycemia and hyperlipidemia, such as diabetes, obesity, steatohepatitis or cardiovascular diseases.

The present disclosure provides a fusion protein. The fusion protein includes R1-R2, R2-R1, R1-L-R2 or R2-L-R1.

R1 is a human fibroblast growth factor FGF19 protein or an FGF19 protein mutant or an active fragment, R2 is glucagon-like peptide-1 (GLP-1) or an analog thereof, exendin-4, or a GLP-1 mutant or an active fragment, and L is a linker peptide.

In one embodiment, the FGF19 protein contains an amino acid sequence as set forth in any one of SEQ ID NO. 1-3, or a protein obtained by substituting or deleting one or more amino acid residues from the amino acid sequences as set forth in SEQ ID NO. 1-3, or a protein derived from SEQ ID NO. 1-3 and having the same biological activity as the amino acid sequences of SEQ ID NO. 1-3; and the glucagon-like peptide-1 contains an amino acid sequence as set forth in SEQ ID NO. 4-5, or a protein obtained by substituting and deleting one or more amino acid residues from the amino acid sequences as set forth in SEQ ID NO. 4-5, or a protein derived from SEQ ID NO. 4-5 and having the same biological activity as the amino acid sequences of SEQ ID NO. 4-5.

In one embodiment, the linker peptide consists of 0-30 amino acids and comprises any one of (a)-(e):

(a) (Gly-Gly-Gly-Gly-Ser)$_n$,-(Ser)$_m$, n may be an integer of 0 to 5, and m is 0 or 1;

(b) (Gly-Gly-Gly-Gly-Ser)$_n$-(Ser-Pro)$_m$, n may be an integer of 0 to 5, and m is 0 or 1;

(c) (Pro-Glu-Ala-Pro-Thr-Asp)$_n$, n may be an integer of 0 to 5;

(d) (Ser-Ser-Ser-Ser-Gly)$_n$-(Ser-Pro)$_m$, n may be an integer of 0 to 5, and m is 0 or 1; and (e) any combination of subparts (a)-(d).

The present disclosure provides a gene encoding a fusion protein with an amino acid sequence as set forth in any one of SEQ ID NO. 1-3.

The present disclosure provides a vector or a microbial cell carrying the gene.

The present disclosure provides use of the fusion protein in preparation of a drug for preventing, relieving and/or treating obesity and complications thereof.

In one embodiment, the obesity and complications thereof include hyperlipidemia, fatty liver, insulin resistance, and glucose intolerance.

In one embodiment, the relieving and/or treating obesity and complications thereof include inhibiting weight gain, reducing blood lipids and blood glucose, and increasing insulin sensitivity.

The present disclosure provides a drug for treating hepatitis or a related disease. The drug takes the fusion protein with an amino acid sequence as set forth in any one of SEQ ID NO. 1-3 as an effective component.

In one embodiment, the drug further includes a pharmaceutically acceptable carrier or excipient.

In one embodiment, the administration routes of the drug include oral administration, intraperitoneal injection, subcutaneous injection, intravenous injection, or intramuscular injection.

In one embodiment, the treating hepatitis or a related disease includes reducing liver weight and the content of liver triglycerides, repairing liver damage, inhibiting expressions of inflammatory factors, and relieving nonalcoholic steatohepatitis, atherosclerosis, liver damage, liver cirrhosis, liver cancer, primary biliary cholangitis, and/or primary sclerosing cholangitis.

The present disclosure provides a drug for improving insulin sensitivity and regulating blood sugar. The drug takes the fusion protein with an amino acid sequence as set forth in any one of SEQ ID NO. 1-3 as an effective component.

In one embodiment, the drug further includes a pharmaceutically acceptable carrier or excipient.

In one embodiment, the administration routes of the drug include oral administration, intraperitoneal injection, subcutaneous injection, intravenous injection, or intramuscular injection.

Beneficial Effects of the Present Disclosure

Compared with an original FGF19 analog and GLP-1, the 3 novel double-target fusion proteins of the present disclosure have a significantly increased half-life period, alleviate side effects of gastrointestinal discomfort and diet decline caused by GLP-1, have a relatively small influence on normal life activities of organisms, and are long-acting, stable and better in treating obesity, overweight, metabolic syndrome, diabetes, hyperglycemia, dyslipidemia, nonalcoholic steatohepatitis (NASH), atherosclerosis, liver injury, liver cirrhosis, liver cancer, primary biliary cholangitis (PBC), and primary sclerosing cholangitis (PSC).

DETAILED DESCRIPTION

Experimental animals and feeding: db/db mice were purchased from Shanghai Slac Company, fed in the Animal Center of Wuxi School of Medicine, Jiangnan University, and illuminated alternately every 12 hours at a temperature of 20±2° C.

Other drugs are analytically pure and made in China.

EXAMPLE 1

Construction, Expression and Purification of Recombinant Proteins (1) Construction of GLP-FGF19-1, GLP-FGF19-2 and GLP-FGF19-3 expression vectors FGF19 with amino acid sequences as set forth in SEQ ID NO. 1, SEQ ID NO. 2 and SEQ ID NO. 3 were respectively fused with GLP-1 as set forth in SEQ ID NO. 4 (FGF19 was connected with GLP-1 by selectively using common protein linker peptides) to obtain 3 novel fusion protein genes GLP-FGF19-1 (as set forth in SEQ ID NO. 6), GLP-FGF19-2 (as set forth in SEQ ID NO. 7), and GLP-FGF19-3 (as set forth in SEQ ID NO. 8), respectively. Corresponding coding gene sequences were designed according to a codon preference of *Escherichia coli*. The 3 genes were synthesized by Shanghai Generay Biotech CO., LTD, and NdeI and BamHI restriction sites were designed at two ends of each gene. 3 synthesized vectors containing respective target gene fragments and pET30a (+) were subjected to double enzyme digestion by NdeI and BamHI respectively, and after the enzyme digestion was finished, required target fragments were subjected gel extraction respectively. 4 target fragments were respectively linked with a prokaryotic expression vector pET30a (+) by using a T4 DNA ligase, with 10 μL of a ligation reaction system, mixed evenly, ligated overnight at 4° C., and then respectively transformed into *E. coli* DH5α. Positive clones were picked. After enzyme digestion identification, 3 recombinant plasmids pET30a-GLP-FGF19-1, pET30a-GLP-FGF19-2 and pET30a-GLP-FGF19-3, were respectively constructed.

(2) Expression and purification of proteins

The recombinant plasmids pET30a-GLP-FGF19-1, pET30a-GLP-FGF19-2, and pET30a-GLP-FGF19-3 containing correct sequences were transformed into an expression strain Rosseta (DE3) competent cell. Transformed single colonies were respectively inoculated into 20 mL of an LB medium containing Kan (50 µg/mL), cultured at 37° C. for 8 h, inoculated into another 20 mL of an LB medium containing Kan (50 µg/mL) at a volume ratio of 1:100, and cultured at 37° C. When A600 was about 0.35, IPTG was added to a final concentration of 0.25 mmol/L for induction at a temperature of 30° C. The bacterial cells were harvested after 5 h, resuspended in a lysis buffer (20 mmol/L Tris, 150 mmol/L NaCl, pH 8.0), disrupted, and centrifuged. A supernatant and a precipitate were respectively taken for a 12 wt % SDS-PAGE analysis. The results showed that the expression of GLP-FGF19-1, GLP-FGF19-2 and pET30a-GLP-FGF19-3 proteins was significantly increased in E. coli. Target proteins were mostly in a form of inclusion bodies.

A large number of the induced bacterial cells were collected, a lysozyme (1 mg/mL) was added into the bacterial cells, and the bacterial cells were placed on ice for 30 min and ultrasonically disrupted (working for 1 s, pausing for 1 s, 4 min/time, 3 cycles in total). After the bacterial cells were completely disrupted, cell disrupted liquid was treated by using a QuixStand pretreatment system (750 kD ultrafiltration hollow fiber column), inclusion bodies were enriched, and liquid from a membrane permeation end was discarded. When the total volume was about 60 mL, the inclusion bodies were washed by adding 100 mL of a wash buffer (20 mmol/L Tris, 2 mol/L urea, 150 mmol/L NaCl, pH 8.0). When the volume of the solution was 50 mL, 100 mL of a washing solution was added thereto, and the above experiment was repeated 4 times. After washing, when the volume of the solution was 50 mL, the permeation end was closed, 150 mL of a denaturation solution (20 mmol/L Tris, 10 mol/L urea, 150 mmol/L NaCl, pH 8.0) was added to the washed inclusion bodies for cyclic denaturation for 2 hours. The permeation end was opened and liquid collected from the membrane permeation end was an mFGF19 denaturation solution. The denatured mFGF19 was concentrated with a 5 KD hollow fiber column until the volume reached 80 mL, and then renaturated. A container containing a renaturation solution (20 mmol/L Tris, 50 mmol/L NaCl, pH 8.0) was connected with a reservoir of the hollow fiber column via a rubber tube. After the reservoir was sealed and the liquid flowed out from the permeation end, the renaturation solution was dropwise added into the denaturation solution at a certain speed due to a negative pressure generated in the reservoir to slowly renature at a constant speed. When the volume of the renaturation solution was 6 times that of the denaturation solution, namely the renaturation was finished, centrifugation was performed at 8,000 rpm/min and 4° C. for 20 min, and a supernatant was collected. After the renatured supernatant was completely bound to a CaptoQ column (packed in an XK16/20 empty column with a height of 10 cm at a flow rate of 300 cm/h) equilibrated with IEX buffer A times the volume of column (20 mmol/L Tris, 10 mmol/L NaCl, pH 8.0) via an AKTA purifier 100 system, the column was rinsed with IEX buffer A 3-4 times the volume of column. When an ultraviolet curve reached a stable baseline, a mixture of IEX buffer A and IEX buffer B (20 mmol/L Tris, 1 mol/L NaCl, pH 8.0) was used for elution, impure proteins were rinsed with and 100 wt % of IEX buffer B, a target protein was eluted with 18.5 wt %-19 wt % of IEX buffer B, and each eluted peak was collected and subjected to 15 wt % SDS-PAGE electrophoretic analysis. The results showed that the protein purity after the purification was 95% or more.

EXAMPLE 2

Detection of in-Vivo Half-Life Periods of Recombinant Proteins

In-vivo half-life periods of 5 proteins FGF19 (an amino acid sequence as set forth in SEQ ID NO. 9), GLP-1 (an amino acid sequence as set forth in SEQ ID NO. 4), GLP-FGF19-1, GLP-FGF19-2, and GLP-FGF19-3 were detected.

25 domestic rabbits of about 2 kg were selected and randomly divided into 5 groups. The rabbits in each group were subcutaneously injected with 5 proteins FGF19, GLP-1, GLP-FGF19-1, GLP-FGF19-2, and GLP-FGF19-3 at a dose of 5 mg/kg. About 800 µL of blood was collected in ear veins at 0 h, 1 h, 3 h, 5 h, 7 h and 24 h after administration. The blood was centrifuged at 12,000 r/m for 10 min and a supernatant was collected and stored at −20° C. for later use. An ELISA indirect method was used to measure in-vivo half-life periods of 5 proteins: FGF19, GLP-1, GLP-FGF19-1, GLP-FGF19-2, and GLP-FGF19-3 proteins with different diluted concentrations (2 µg/mL, 0.2 µg/mL, 200 ng/mL, 20 ng/mL, and 2 ng/mL) were respectively used to establish a standard curve of protein concentration content. The diluted standard proteins and serums were used to coat ELISA plates, the content of the target protein in each serum was measured by the ELISA indirect method, and the in-vivo half-life periods of 5 proteins were statistically analyzed and calculated.

In-vivo half-life period $$t_{1/2} = \frac{0.301 * (t2 - t1)}{\log(OD1/OD2)},$$

wherein OD1 and OD2 represent an average light absorption value on an ELISA plate corresponding to the serum taken at t1 and t2, respectively.

Figure 1:
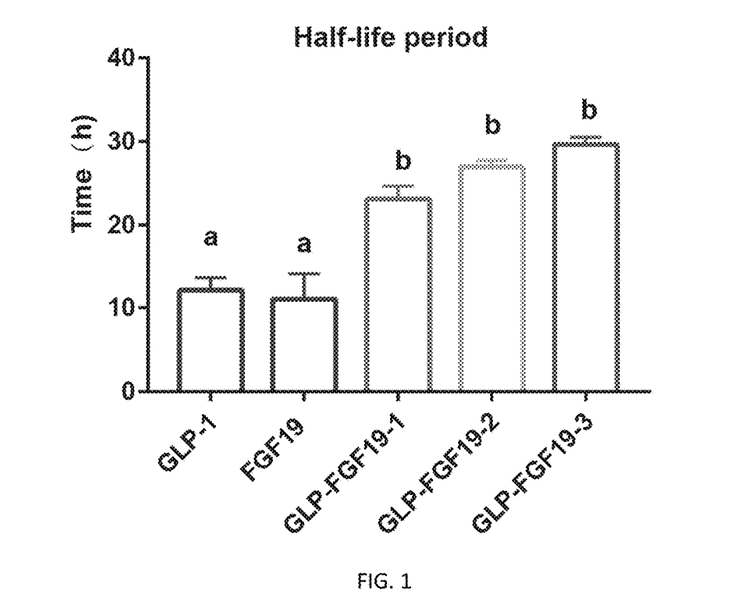
FIG. 1 shows comparison of an in-vivo half-life period of 5 proteins.

The results are shown in FIG. 1. The in-vivo half-life periods of FGF19, GLP-1, GLP-FGF19-1, GLP-FGF19-2, and GLP-FGF19-3 are calculated by the formula to be about 10 h, 6 h, 24 h, 23 h, and 24 h respectively, indicating that the in-vivo half-life periods of the 3 novel GLP-FGF19-1, GLP-FGF19-2, and GLP-FGF19-3 were significantly increased.

EXAMPLE 3

Effects of Recombinant Proteins on Body Weight, Diet, Blood Lipids, and Diabetes-Related Indicators 3 proteins GLP-FGF19-1, GLP-FGF19-2, and GLP-FGF19-3 were prepared according to the method of Example 1.

50 SPF-grade 8-week-old male db/db mice were taken, pre-fed for 1 week, weighed, and fasted for 6 hours the next day with free feeding of water. Blood was taken from tail veins for measuring fasting blood glucose of the mice. The mice with abnormal body weight were excluded, and 36 molded mice with blood glucose and weight values close to mean values were screened and randomly divided into a saline group, an FGF19 group, a GLP-1 group, a GLP- FGF19-1 group, a GLP-FGF19-2 group, and a GLP-FGF19-3 group, with 6 mice in each group. Corresponding test substances were intraperitoneally injected into the experimental groups once at about half past eight every morning at a dose of 2 mg/kg. Saline of the same volume was injected into the saline group. The administration was performed continuously for 8 weeks. During the experiment process, the mice could eat and drink water freely. During the period, the diet and body weight status of the mice were monitored. After 8 weeks of administration, the mice in each experimental group were sacrificed (fasted overnight). Blood was taken from eyeballs for measuring the levels of blood glucose, triglycerides (TG), and total cholesterol (TC) of the experimental mice. The obtained experimental data was statistically analyzed.

Figure 2:
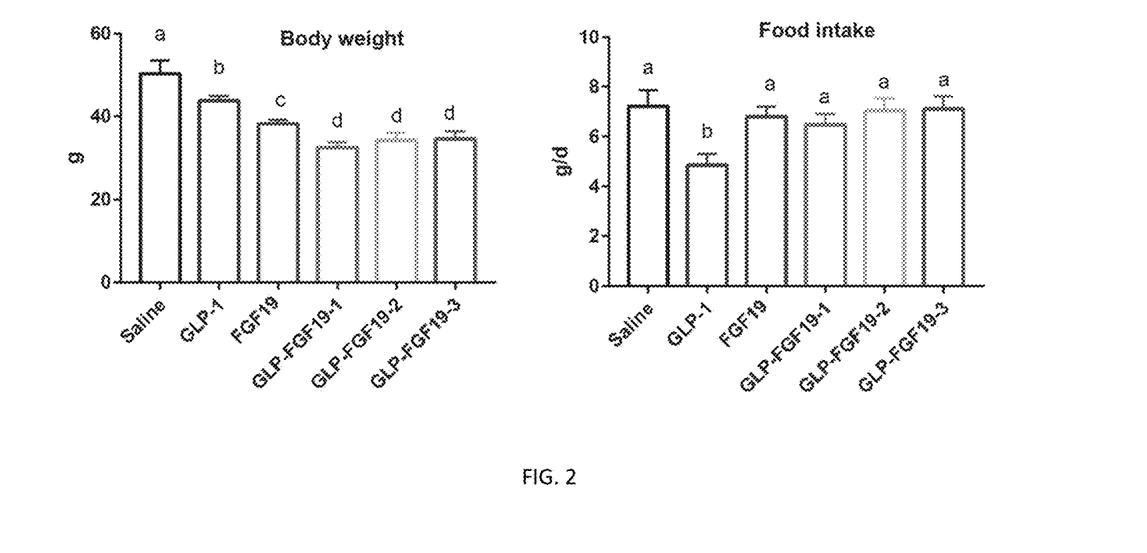
FIG. 2 shows effects of 5 proteins on body weight and diet of db/db mice.
Figure 3:
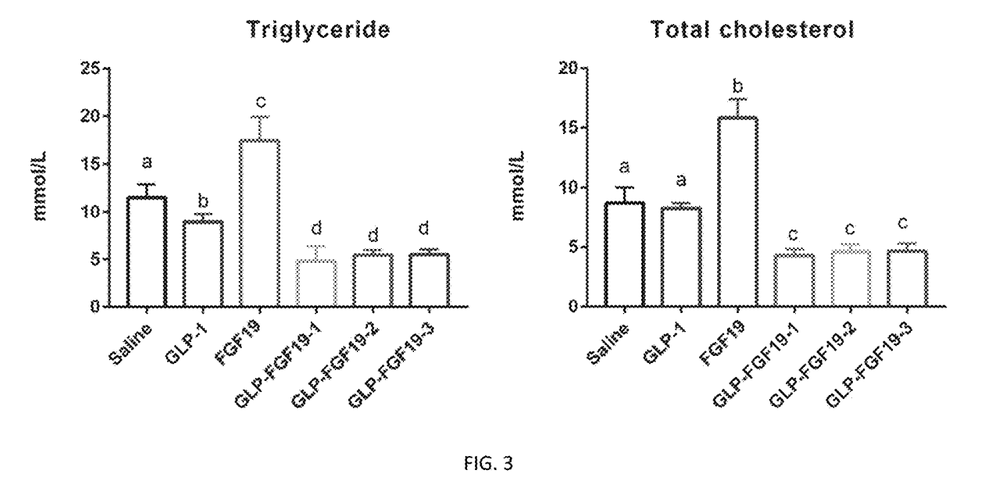
FIG. 3 shows effects of 5 proteins on blood lipids in db/db mice.
Figure 4:
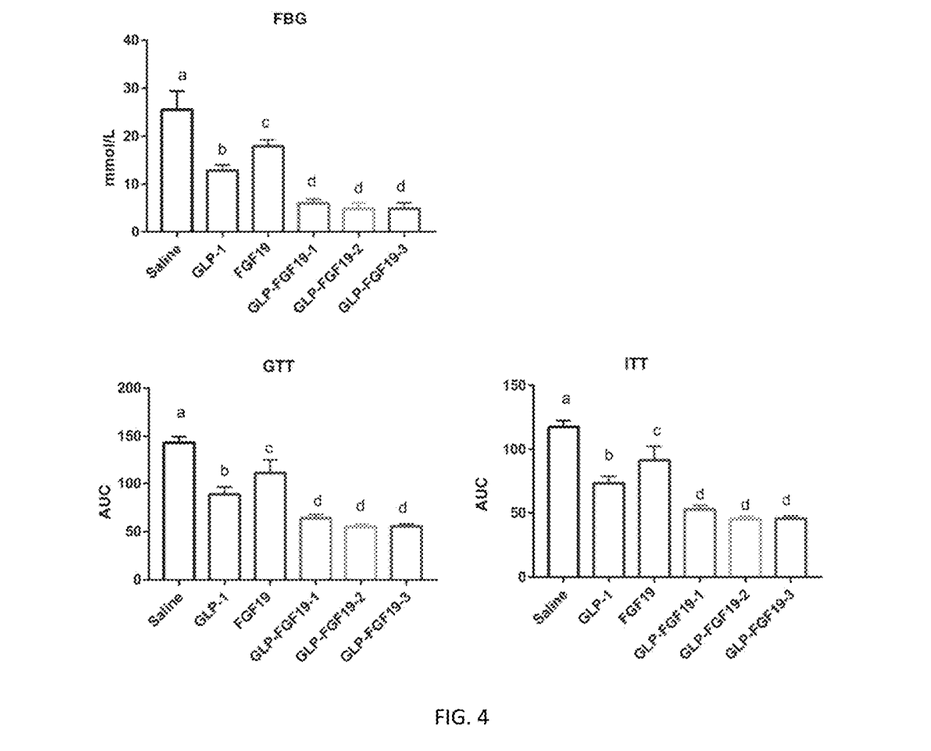
FIG. 4 shows effects of 5 proteins on diabetes-related indicators in db/db mice.
Figure 5A:
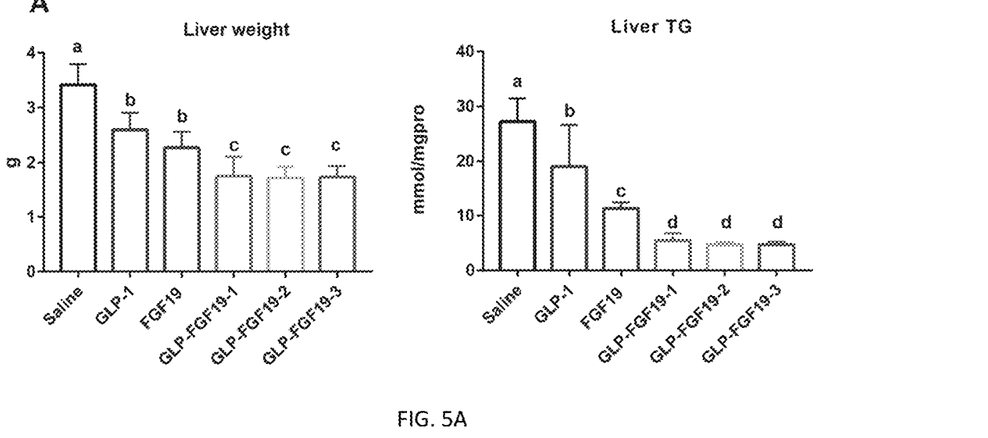
FIG. 5A shows liver weight and liver triglyceride (TG) content of mice.
Figure 5B:
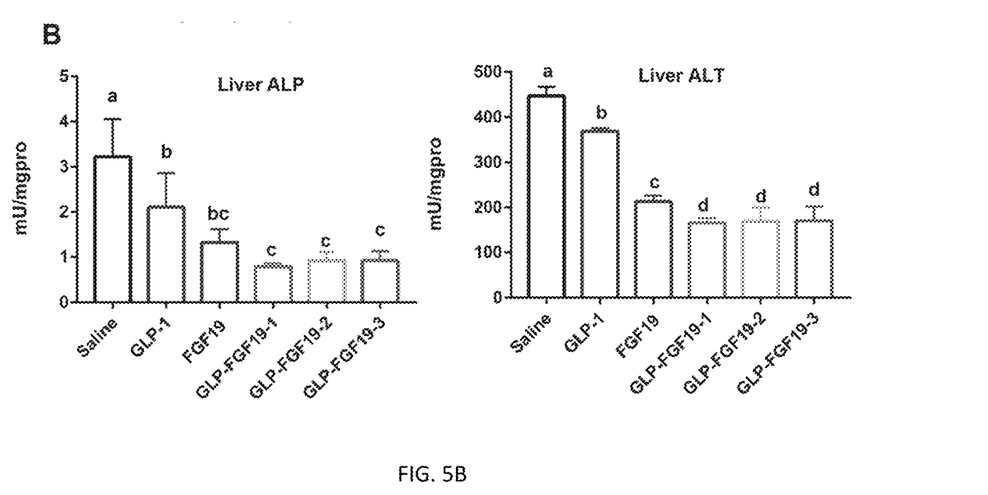
FIG. 5B shows alkaline phosphatase content and glutamic-pyruvic transaminase content.
Figure 5C:
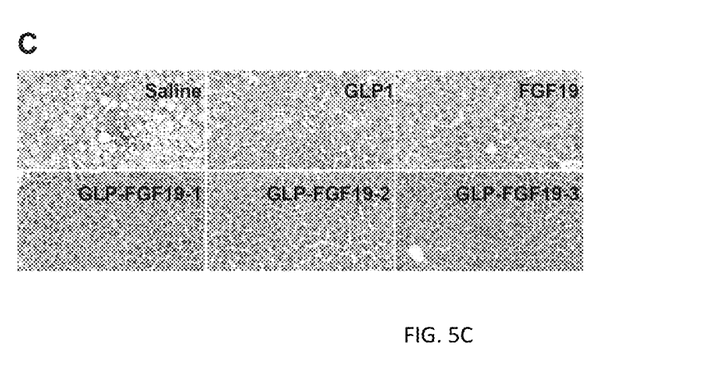
FIG. 5C show HE staining of tissue sections.
Figure 5D:
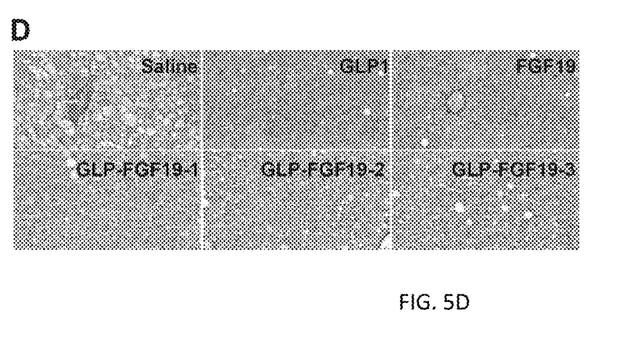
FIG. 5D shows sirius red staining of tissue sections.

The experimental detection data is shown in FIGS. 2-4. The results in FIG. 2 show that compared with the saline group, the body weight of the mice can be remarkably reduced by the FGF19 protein, GLP-1 and the 3 novel proteins GLP-FGF19-1, GLP-FGF19-2, and GLP-FGF19-3, but the diet of the mice can be remarkably reduced and the appetite of the mice can be inhibited after the injection of the GLP-1 protein. However, compared with GLP-1, the 3 novel proteins GLP-FGF19-1, GLP-FGF19-2, and GLP-FGF19-3 can more remarkably inhibit the body weight after administration, without affecting the feeding of the mice, indicating that such fusion modification successfully alleviates a side effect of diet decline caused by the original GLP-1.

After 8 weeks of administration, the results of blood lipid levels in the serums of the mice in each experimental group are shown in FIG. 3. Compared with the saline group, the 5 proteins FGF19, GLP-1, GLP-FGF19-1, GLP-FGF19-2, and GLP-FGF19-3 can significantly reduce the content of triglycerides and total cholesterol in the serums after injection. However, the treatment effects of GLP-FGF19-1, GLP-FGF19-2, and GLP-FGF19-3 are better than those of the original GLP-1 and FGF19.

After 8 weeks of administration, the results of fasting blood glucose, insulin sensitivity, and glucose tolerance of the mice in each experimental group are shown in FIG. 4. Compared with the saline group, the 5 proteins FGF19, GLP-1, GLP-FGF19-1, GLP-FGF19-2, and GLP-FGF19-3 can significantly ameliorate blood glucose and insulin resistance after injection. However, the treatment effects of GLP-FGF19-1, GLP-FGF19-2, and GLP-FGF19-3 are better than those of the original GLP-1 and FGF19.

EXAMPLE 4

Effect of Recombinant Proteins on Nonalcoholic Steatohepatitis (NASH)-Related Indicators 3 proteins GLP-FGF19-1, GLP-FGF19-2, and GLP-FGF19-3 were prepared according to the method of Example 1.

60 SPF-grade 8-week-old male C57BL/6 mice were taken, pre-fed for 1 week, and fed with a methionine/choline-deficient (MCD) feed. After 8 weeks of administration, the mice with abnormal body weight were excluded, and 36 molded mice with blood glucose and weight values close to mean values were screened and randomly divided into a saline group, an FGF19 group, a GLP-1 group, a GLP-FGF19-1 group, a GLP-FGF19-2 group, and a GLP-FGF19-3 group, with 6 mice in each group. Corresponding test substances were intraperitoneally injected into the experimental groups once at about half past eight every morning at a dose of 2 mg/kg. Saline of the same volume was injected into the saline group. The administration was performed continuously for 8 weeks. During the experiment process, the mice could eat and drink water freely. After 8 weeks of administration, the mice in each experimental group were sacrificed (fasted overnight) for measuring the levels of liver triglycerides (TG), an alkaline phosphatase (ALP), and a glutamic-pyruvic transaminase (ALT) of the experimental mice. Tissue sections were stained and inflammation indicators were detected. The obtained experimental data was statistically analyzed.

The experimental detection data is shown in FIG. 5. The results in FIG. 5A show that compared with the saline group, FGF19, GLP-1, GLP-FGF19-1, GLP-FGF19-2, and GLP-FGF19-3 can all significantly reduce the liver weight and the content of liver triglycerides (TG) of the mice. However, the treatment effects of GLP-FGF19-1, GLP-FGF19-2, and GLP-FGF19-3 are better than those of the original GLP-1 and FGF19. The transaminase result in FIG. 5B further show that the 3 novel proteins GLP-FGF19-1, GLP-FGF19-2, and GLP-FGF19-3 have a significantly better protective function on liver damage than the original FGF19 and GLP-1. In addition, HE staining results directly show that GLP-FGF19-1, GLP-FGF19-2, and GLP-FGF19-3 can significantly reduce liver fat vacuoles after injection, with virtually no vacuoles observed microscopically. However, after treatment with FGF19 and GLP-1, there are still some fat vacuoles (FIG. 5C). FIG. 5D show sirius red staining results to observe deposition of liver collagen fibers to reflect liver fibrosis. The results show that the mutation-modified 3 novel proteins GLP-FGF19-1, GLP-FGF19-2, and GLP-FGF19-3 can reverse liver fibrosis. After treatments with FGF19 and GLP-1, there will still be some fibrosis, indicating that the reversing effects of the modified recombinant proteins on liver fibrosis are significantly better than those of the original proteins. The detection of the multiple indicators shows that the treatment effects of the 3 novel proteins GLP-FGF19-1, GLP-FGF19-2, and GLP-FGF19-3 after fusion modification on the NASH and liver damage are significantly better than those of the control.

Although the present disclosure has been disclosed as above in the preferred examples, it is not intended to limit the present disclosure. Any person familiar with the art can make various changes and modifications without departing from the spirit and scope of the present disclosure. Therefore, the protection scope of the present disclosure should be as defined in the claims.

What is claimed is:

1. A fusion protein, comprising:
R1-R2 or R1-L-R2 or R2-R1 or R2-L-R1,
wherein:
R1 is a human fibroblast growth factor 19 (FGF19) protein;
R2 is a glucagon-like peptide-1 (GLP-1) or exendin-4;
L is a linker peptide;
the FGF19 protein has the amino acid sequence as set forth in any one of SEQ ID NO: 2 and 3; and
the GLP-1 has the amino acid sequence as set forth in SEQ ID NO:4 or 5.

2. A method of treating hepatitis or a related disease comprising:
administering to a subject in need thereof an effective amount of a composition comprising the fusion protein of claim 1,
wherein the treating hepatitis or a related disease comprises reducing liver weight, reducing liver triglycerides, repairing liver damage, relieving nonalcoholic steatohepatitis, relieving atherosclerosis, relieving liver damage, relieving primary biliary cholangitis, and/or relieving primary sclerosing cholangitis.

3. The method of claim 2, wherein the composition is administered orally, by intraperitoneal injection, by subcutaneous injection, by intravenous injection, or by intramuscular injection.

4. A method of improving insulin sensitivity and regulating blood sugar, comprising:
   administering to a subject in need thereof an effective amount of a composition comprising the fusion protein of claim 1.

5. The method of claim 4, wherein the composition is administered orally, by intraperitoneal injection, by subcutaneous injection, by intravenous injection, or by intramuscular injection.

6. The fusion protein of claim 1, wherein L consists of 0 to 30 amino acids, and wherein L is one of (a) to (e):
   (a) (Gly-Gly-Gly-Gly-Ser)$_n$-(Ser)$_m$, wherein n is an integer of 0 to 5, and m is 0 or 1;
   (b) (Gly-Gly-Gly-Gly-Ser)$_n$-(Ser-Pro)$_m$, wherein n is an integer of 0 to 5, and m is 0 or 1;
   (c) (Pro-Glu-Ala-Pro-Thr-Asp)$_n$, wherein n is an integer of 0 to 5;
   (d) (Ser-Ser-Ser-Ser-Gly)n-(Ser-Pro)$_m$, wherein n is an integer of 0 to 5, and m is 0 or 1; and
   (e) any combination of subparts (a)-(d).

7. The fusion protein of claim 1, wherein the fusion protein has a half life in vivo of 20 hours or more.

8. The fusion protein of claim 1, wherein R2 is exendin-4.

9. The fusion protein of claim 1, wherein R1 has the amino acid sequence as set forth in SEQ ID NO:2.

10. The fusion protein of claim 9, where R2 is GLP-1.

11. The fusion protein of claim 1, wherein R1 has the amino acid sequence as set forth in SEQ ID NO:3.

12. The fusion protein of claim 11, wherein R2 is GLP-1.

* * * * *